United States Patent [19]

Naegeli

[11] Patent Number: 5,416,069

[45] Date of Patent: May 16, 1995

[54] NAPTHOFURAN DERIVATIVES USEFUL IN ODORANT AND FLAVORANT COMPOSITIONS AND PROCESS FOR THEIR PRODUCTION

[75] Inventor: Peter Naegeli, Wettingen, Switzerland

[73] Assignee: Givaudan-Roure Corporation, Clifton, N.J.

[21] Appl. No.: 275,213

[22] Filed: Jul. 14, 1994

[30] Foreign Application Priority Data

Jul. 23, 1993 [CH] Switzerland .......................... 2234/93

[51] Int. Cl.$^6$ .................. C07D 307/92; A24B 15/28; A61K 7/46
[52] U.S. Cl. .................................. 512/13; 426/536; 549/458; 131/277
[58] Field of Search .................... 549/458; 512/13; 426/536

[56] References Cited

U.S. PATENT DOCUMENTS

| | | | |
|---|---|---|---|
| 4,341,908 | 7/1982 | Willis et al. | 568/819 |
| 4,613,710 | 9/1986 | Buchi et al. | 568/819 |
| 4,633,011 | 12/1986 | Buchi et al. | 560/119 |
| 4,677,233 | 1/1987 | Buchi et al. | 568/819 |
| 5,268,355 | 12/1993 | Snowden et al. | 549/458 |

FOREIGN PATENT DOCUMENTS 0170955 12/1986 European Pat. Off. .
680444 8/1992 Switzerland .
WO-A-8200030 1/1982 WIPO .

OTHER PUBLICATIONS

Olhoff, G., "Fragrance Chemistry" Ed. E. T. Thiemer, 1982, Academic Press, pp. 535–571.
Bauer et al., "Common Fragrance and Flavor Materials," (1985) VCH Verlagsgesellschaft, Weinheim pp. 1–5.

*Primary Examiner*—Bernard Dentz
*Attorney, Agent, or Firm*—George M. Gould; George W. Johnston; Mark E. Waddell

[57] ABSTRACT

Novel naphthofuran derivatives of the formula

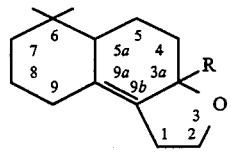

I wherein R represents hydrogen, methyl or ethyl. The compounds of formula I are valuable (amber) odorants and also flavorants. Odorant and flavorant compositions employing (I) as well as processes for making them are also described.

9 Claims, No Drawings

NAPTHOFURAN DERIVATIVES USEFUL IN ODORANT AND FLAVORANT COMPOSITIONS AND PROCESS FOR THEIR PRODUCTION

The present invention is concerned with novel naphthofuran derivatives of the general formula

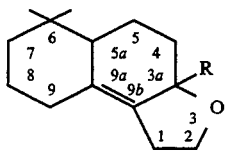

wherein R represents hydrogen, methyl or ethyl.

The novel compounds of formula I are valuable amber odorants and the invention is accordingly also concerned with the use of these odorants in perfume and flavorant compositions. Moreover, the invention is concerned with the manufacture of the compounds of formula I and with the aforementioned perfume and flavorant compositions.

Formula I above embraces all stereoisomers, i.e. inter alia the stereoisomeric compounds of formulae Ia and Ib hereinafter as well as their respective enantiomers:

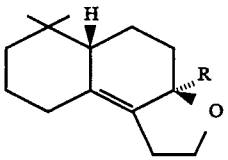

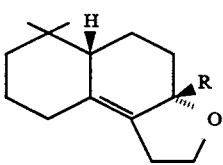

wherein R has the above significance.

The sensoric properties of the compounds of formula I fall into the domain of amber substances.

From the structural class of hydrogenated naphtho[2,1-b]-furans a number have already been described in the literature, for example by G. Ohloff in "Fragrance Chemistry" Ed. E. T. Theimer, 1982, Academic Press, pages 535 et seq. However, from this structural class only AMBROX ® (Ohloff, loc. cit, compound 75) by virtue of its olfactory strength and also in part because of its nature identity, has hitherto been very much in demand on the odorant market and has been used in large amounts. This product characterizes the typical warm-woody-tobacco-like partial aspects of ambergris, which is a very scarce and expensive natural material.

There is accordingly a need to find and to develop additional, strong amber substances; as far as possible those which also have the other olfactory nuances of ambergris without lacking its tenacity (for a description of the odor of ambergris, see Ohloff, above).

Such compounds, i.e. amber substances, are now made available in accordance with the invention by the compounds of formula I above. It has surprisingly been found that these compounds not only attain the olfactory strength of e.g. AMBROX ® very well, but also olfactorily reproduce the total aspect of ambergris very typically.

The compounds of formula I in accordance with the invention can be used in a wide range of odorant compositions for perfumery, cosmetics and also for flavors, especially tobacco flavors. They mix well, i.e. they harmonize, with all known materials which are used in perfumery and flavor compositions, such as, for example:

Natural products, such as, for example, tree moss absolute, basil oil, tropical fruit oils (such as bergamot oil, mandarine oil, etc.), mastix absolute, myrtle oil, palmarosa oil, patchouli oil, petitgrain oil, wormwood oil, lavender oil, rose oil, jasmin oil, ylang-ylang oil or sandalwood oil etc.;

alcohols, such as farnesol, geraniol, linalool, nerol, phenylethyl alcohol, rhodinol, cinnamic alcohol, cis-3-hexenol, menthol, α-tocopherol etc.;

aldehydes, such as citral, α-hexyl cinnamaldehyde, hydroxycitronellal, LILIAL ®, (p-tert.butyl-α-methyl-di-hydrocinnamaldehyde), methylnonylacetaldehyde, phenylacetaldehyde, anisaldehyde, vanillin etc.;

ketones, such as allylionone, α-ionone, β-ionone, isoraldein (isomethyl-α-ionone), verbenone, nootkaton, geranylacetone etc.;

esters, such as allyl phenoxyacetate, benzyl salicylate, cinnamyl propionate, citronellyl acetate, decyl acetate, dimethylbenzylcarbinyl acetate, ethyl acetoacetate, ethyl acetylacetate, cis-3-hexenyl isobutyrate, linalyl acetate, methyl dehydrojasmonate, styrallyl acetate, vetiveryl acetate, benzyl acetate, cis-3-hexenyl salicylate, geranyl acetate etc.;

lactones, such as γ-undecalactone, δ-decalactone, pentadecan-15-olide etc.;

acetals, such as VIRIDIN ® (1,1-dimethoxy-2-phenylethane) etc.;

various components often used in perfumery, such as indole, p-menthane-8-thiol-3-one, methyleugenol, eugenol, anethol etc.

The compounds of formula I can be used within wide limits which can range e.g. from about 0.01 to about 90 wt. %. The concentrations preferably lie between about 0.1 and about 5 wt. % for odorant compositions. As components for flavor compositions the compounds of formula I can be used e.g. for improving, modifying and/or intensifying fruit flavors or also as woody and tobacco-like flavors for foodstuffs and luxury consumables, in which case the concentration in the final product preferably lies in the range of about 0.01 to about 500 ppm (parts per million).

As mentioned, the compounds I can be used in the manufacture of odorant and flavor compositions using a wide range of known odorants and odorant mixtures or flavorants. In the manufacture of such compositions the known odorants, odorant mixtures and flavorants set forth above can be used in a manner known per se.

The compounds of formula I in accordance with the invention can be manufactured according to Reaction Scheme I hereinafter. In the formulae given in this Scheme, R has the significance given above and R¹ signifies lower alkyl, preferably straight-chain or branched alkyl groups with 1 to 6 carbon atoms, such as methyl, ethyl, propyl, isopropyl, butyl, isobutyl, tert.butyl and the like.

The compounds of formula IV in which R¹ has the foregoing significance, which are used as starting materials, are novel compounds and are also an object of the present invention. They can be prepared as shown in Schemes II and III. The compounds of formulae IIIa, IIIb and IIa given in Schemes II and III are also novel compounds and are accordingly objects of the present invention.
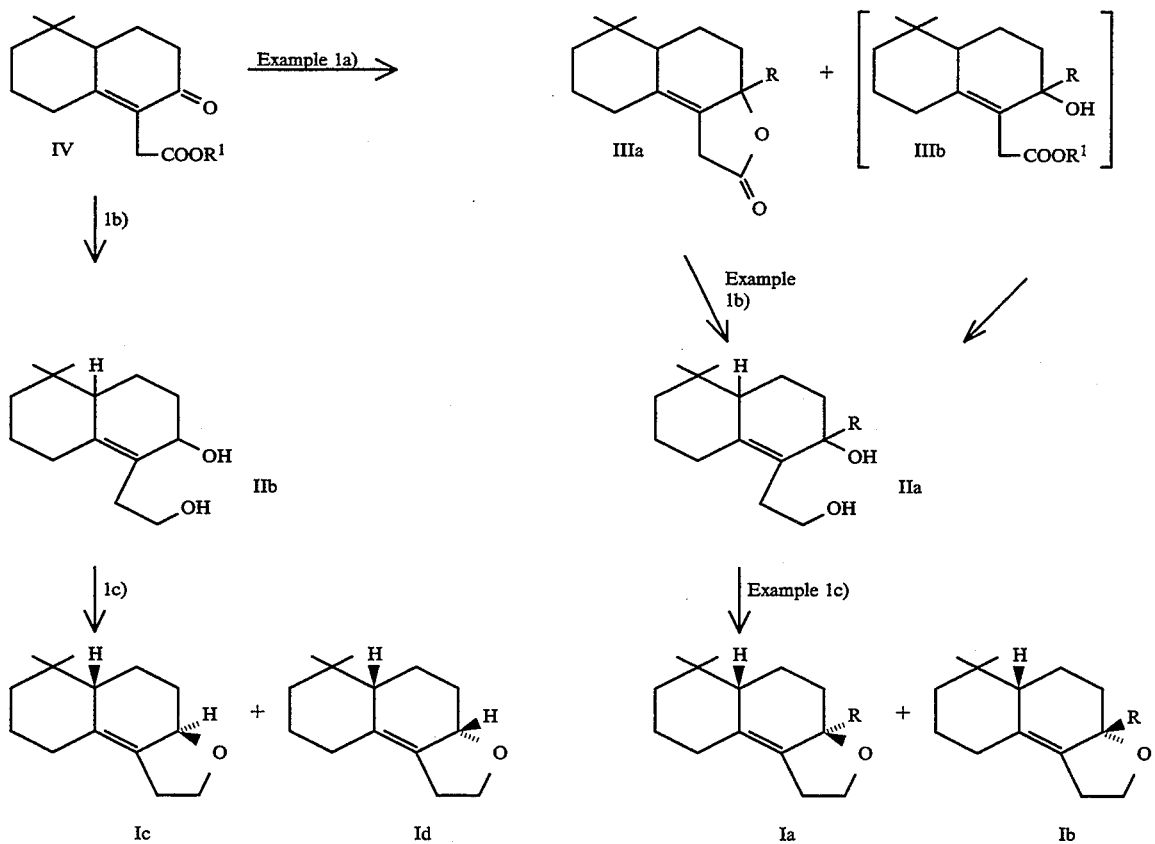
Scheme I
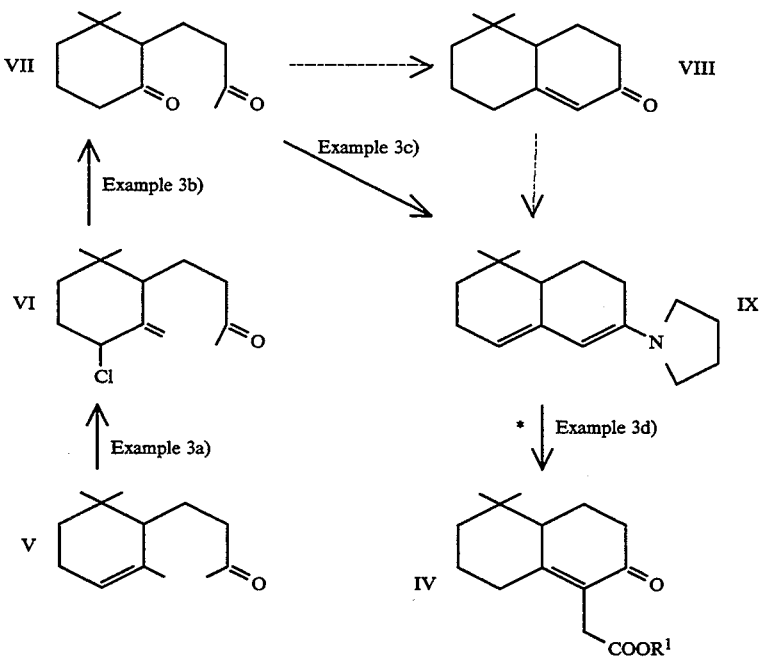
Scheme II
*includes an unobvious alkylation step

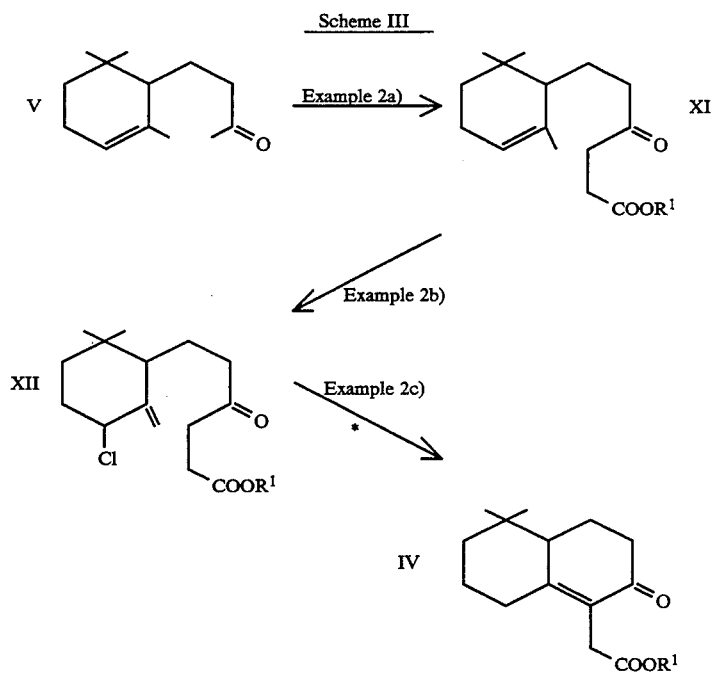

Scheme III

*includes an unobvious (one pot) step:
ozonisation of the double bond, reduction of the chloroozonide and
aldolisation of the so-formed diketo ester The following Examples are for illustrative purposes only, there being no intention to limit the scope of the invention except as set forth in the claims which follow. All reactions were carried out under an inert gas. The temperatures are given in ° Celsius.

EXAMPLE 1 a) 30 g (103 mmol) of tert.butyl 2-[5,5-dimethyl-2-oxo-2,3,4,4a,5,6,7,8-octahydronaphth-1-yl]-acetate was placed in 530 ml of 1,2-dimethoxyethane under argon in a 1.5 l four-necked flask fitted with a stirrer, thermometer, condenser and septum stopper. The solution was cooled to −30° and treated within 10 minutes at −30° to −20° with 154 ml (154 mmol) of methyllithium solution (1N in ether). The mixture obtained was stirred at −30° and after 3 hours a further 15.4 ml (15.4 mmol) of methyllithium solution was added dropwise and the cooling bath was removed. After 22 hours the reaction solution was poured into about 1.5 l of saturated NH4Cl solution, whereby the previously dark red solution became yellow. Thereupon, the phases were separated and the aqueous phase was extracted three times with hexane. The combined organic phases were washed with water and with saturated NaCl solution, dried over MgSO4 and evaporated. There was obtained 23.57 g of crude product in the form of a dark yellow oil which was purified by chromatography on silica gel. There was thus obtained a pure 1:1 mixture of (3aRS,-5aSR)- and -(3aSR,5aSR)-3a,6,6-trimethyl-1,2,3a,4,5-,5a,6,7,8,9-decahydronaphtho[2,1 -b]furan-2-one.

NMR (400 MHz) CDCl3+TMS f. peak 1:inter alia 3.17 ppm (1H, split d, J=20); 1.40 ppm (9H,s); 1.006 ppm (3H,s); 0.793 ppm (3H,s)

NMR (400 MHz) CDCl3+TMS f. peak 2: inter alia 3.11 ppm (1H,d,J=20); 2.035 ppm (1H,dt,J1=11,J2=4); 1.415 ppm (9H, split s); 0.95 ppm (3H,s); 0.747 ppm (3H,s).

b) 3.8 g (98 mmol) of LiAlH4 was placed in 100 ml of diethyl ether under argon in a 1.5 l four-necked flask fitted with a stirrer, thermometer, reflux condenser and dropping funnel. Then, 23 g (98 mmol) of the mixture prepared according to a) in 500 ml of diethyl ether was added dropwise within 25 minutes. Thereupon, the grey suspension was heated under reflux for 2 hours, then cooled in an ice bath and hydrolyzed with 200 ml of saturated K2CO3 solution. After phase separation the aqueous phase was extracted three times with ether. The combined organic phases were washed neutral with saturated NaCl solution and water, dried over MgSO4 and evaporated. 21.23 g of a diastereomer mixture of 1-(2-hydroxyethyl)-2,5,5-trimethyl-2,3,4,4a, 5,6,7,8-octahydronaphthalen-2-ol was obtained as a yellow, highly viscous oil.

IR (film): 3320 (str.), 1460(m), 1390+1370(w), 1140(m), 1070+1040(m) cm−1

IR (CHCl3): 3600(m), 3380(str.), 1450(str.), 1380+1360(m), 1260(str.), 1060+1040(str.) cm−1.

The two diasteromers were obtained in pure, crystalline form after separation by chromatography on silica gel (ether:hexane=4:1):

Apolar epimer (m.p. 82°-88° C.) (CH3 and H cis) NMR (CDCl3+TMS, 200 MHz): 3.80 ppm (1H,ddd,J1=10, J2=5, J3=4,5); 3.55 ppm (1H,td,J1=10, J2=4,5); 1.315 ppm (3H,s); 0.98 ppm (3H,s); 0.80 ppm (3H,s):

Polar epimer (m.p. 116°-130° C.) (CH3 and H trans) NMR (CDCl3+TMS, 200 MHz): 3.75 ppm (1H,ddd,J1=10, J2=6, J3=4); 3.60ppm (1H,td,J1=10,J2=5); 1.26 ppm (3H,s); 0.92 ppm (3H,s); 0.73 ppm (3H,s)

c) 21 g (88 mmol) of the diastereomer mixture prepared according to b) was placed in 600 ml of methylene chloride under nitrogen in a 1.5 l four-necked flask fitted with a stirrer, thermometer, condenser and dropping funnel and cooled in an ice bath. Then, 7.2 ml (88 mmol) of methanesulphonyl chloride in 300 ml of pyridine was added dropwise at 5°–7° within 25 minutes and the mixture was stirred at 5°. After 2.5 hours the orange colored solution was poured into 750 ml of water and the phases were separated. The aqueous phase was extracted twice with ether. The combined organic phases were washed twice with water, with cold 6N $H_2SO_4$ to pH=1, twice with water, once with saturated $NaHCO_3$ solution and twice with saturated NaCl solution, dried over $MgSO_4$, filtered and evaporated. 21.05 g of crude product was obtained in the form of a dark orange oil. The crude product was dissolved in 350 ml of 2N KOH in methanol and heated under reflux. After 2 hours the solution was diluted with 200 ml of water and extracted 5 times with 100 ml of hexane each time. The combined organic phases were washed neutral with saturated NaCl solution, dried over $MgSO_4$, filtered and evaporated. 17.44 g of a 1:1 mixture of (3aRS,-5aSR)- and (3aSR,5aSR)-3a,6,6-trimethyl-1,2,3a,4,5-,5a,6,7,8,9-decahydro-naphtho[2,1-b]furan was obtained as a dark yellow oil with the odor of ambergris.

The two pure isomers (cis and trans compound) were prepared as previously described from the two pure diastereomers according to b).

Cis compound: 3a$\beta$,6,6-Trimethyl-1,2,3a,4,5-,5a$\beta$,6,7,8,9-decahydro-naphtho[2,1-b]furan.

$^{13}$C-NMR ($CDCl_3$): 3×q at 30.744, 22.624 and 21.290 ppm; 7×t at 64.189, 42.379, 33.618, 31.496, 27.625, 22.432, 20.700 ppm; d at 44.016 ppm; 4×s at 134.744, 127.878, 78.488 and 36.477 ppm.

$^1$H-NMR: 400 MHz ($CDCl_3$+TMS): 3.99 ppm (1H,ddd,$J_1$=9, $J_2$=9, $J_3$=6); 3.89 ppm (1H,ddd,$J_1$=9, $J_2$=9, $J_3$=6); 2.65 ppm (1H,d of t,$J_1$=15, $J_2$=7); d,J=14); 1.86 ppm (1H,d,ps.t,$J_1$=14, $J_2$=3); 1.13 ppm (3H,split s); 0.986 ppm (3H,s); 0.785 ppm (3H,s).

Trans compound: 3a$\alpha$,6,6-Trimethyl-1,2,3a,4,5-,5a$\beta$,6,7,8,9-decahydronaphtho[2,1-b]furan.

MS: m/e=220(1), 205(100), 190(1), 177(3), 163(4), 149(6), 121(4), 105(5), 91(7), 79(5), 69(13), 55(6), 43(15).

IR (film): 1450+1435(m), 1380(w), 1360(m), 1210(w), 1135(m), 1030(str) cm$^{-1}$.

$^{13}$C-NMR ($CDCl_3$): 3×q at 29.20, 22.996, 19.905 ppm; d at 47.532 ppm; 7×t at 63.881, 42.120, 35.141, 30.745, 27.669, 22.382, 20.916 ppm; 4×s at 134.275, 128.449, 78.187, 34.875 ppm. $^1$H-NMR: 400 MHz ($CDCl_3$+TMS): 3.97 ppm (1H,ddd,$J_1$=8.5, $J_2$=8.5, $J_3$=3.835 ppm (1H,ddd,$J_1$=8.5, $J_2$=8.5, $J_3$=6); 2.35 ppm (1H,dq, $J_1$=13, $J_2$=2); in each case 3H (s) at 1.15, 0.93, 0.733 ppm.

The following compounds can also be prepared in a manner analogous to the foregoing by reducing tert.butyl 2-[5,5-dimethyl-2-oxo-2,3,4,4a,5,6,7,8-octahydronaphth-1-yl]-acetate and cyclizing the diols obtained:

Cis compound: 6,6-Dimethyl-1,2,3a$\beta$,4,5,5a$\beta$,6,7,8,9-decahydronaphtho[2,1 -b]furan.

Trans compound: 6,6-Dimethyl-1,2,3a$\alpha$,4,5,5a$\beta$,6,7,8,9-decahydronaphtho2,1-b]furan.

EXAMPLE 2

The tert.butyl 2-[5,5-dimethyl-2-oxo-2,3,4,4a,5,6,7,8-octahydronaphth-1-yl]-acetate used as the starting material in Example 1 can be prepared as follows:

a) 48 ml (0.36 mol) of diisopropylamine was placed in 800 ml of tetrahydrofuran under argon in a 1.5 l four-necked flask fitted with a stirrer, thermosensor, condenser and septum stopper and the solution was cooled with an isopropanol/dry ice cooling bath. Then, 222 ml (0.36 mol) of butyllithium solution (1.6M in hexane) was added at −70° and thereafter the cooling bath was removed for about 0.5 hour. Subsequently, the mixture was again cooled and 75 ml (0.43 mol) of hexamethylphosphortriamide was added at −70°. After 20 minutes 58.35 g (0.30 mol) of dihydro-$\alpha$-ionone dissolved in a small amount of tetrahydrofuran was added dropwise at −75° to −72°. After a further 1 hour 175.5 g (0.90 mol) of tert.butyl bromoacetate was added dropwise at −75° to −50° within 3 minutes. After about 70 minutes at −70° the reaction mixture was poured into a saturated $NH_4Cl$ solution (∼1.5 l), the phases were separated and the aqueous phase was extracted 4 times with hexane. The combined organic phases were washed neutral with saturated NaCl solution, dried over $MgSO_4$, filtered and evaporated on a rotary evaporator. 201.47 g of crude product was obtained as a pale yellow liquid. After two-fold distillation using a short-path film evaporator in order to remove tert.butyl bromoacetate 87.34 g of tert.butyl 6-(2,6,6-trimethylcyclohex-2-en-1 -yl)-4-oxo-hexanoate was obtained as a yellow oil.

NMR ($CDCl_3$+TMS) (400 MHz): 5.33 ppm (1H,m); 2.66 ppm (2H,dd,J=6) and 2.49 ppm (2H,dd,J=6); 2.47 ppm (1H,dd,$J_1$=8,$J_2$=6); 1.965 ppm (2H,m); 1.67 ppm (3H,split s); 1.44 ppm (9H,s); 1.13 ppm (1 H,dt,$J_1$=13, $J_2$=5); 0.92 and 0.87 ppm (in each case broad 3H,s).

b) 172 g (0.56 mol) of the ketoester prepared according to a) was placed in 1.6 l of methylene chloride in a 6 l four-necked flask fitted with a stirrer, thermometer, condenser and dropping funnel and treated with 330 g (2.3 mol) of potassium dihydrogen phosphate dissolved in 1.6 l of deionized water. The resulting mixture was cooled in an ice bath and then 406 ml (0.58 tool) of sodium hypochlorite solution (∼11%) was added dropwise at 10°–11° within 35 minutes. Subsequently, the mixture was stirred in an ice bath for a further 3 hours. Then, the phases were separated and the aqueous phase was extracted with $CH_2Cl_2$. The combined organic phases were washed with water, saturated $NaHCO_3$ solution and again with water, dried over $MgSO_4$, filtered and evaporated on a rotary evaporator at a maximum bath temperature of 30°. 193.13 g of tert.butyl 6-(2-methylidene-6,6-dimethyl-3-chlorocyclohex-1-yl)-4-oxo-hexanoate was obtained as a yellow oil.

NMR: 200 MHz ($CDCl_3$+TMS): 5.34 ppm and 4.78 ppm (in each case 1H, broad s); 4.475 ppm (1H,dd,$J_1$=7,$J_2$=5); 1.44 ppm (9H,s); 0.94 and 0.855 ppm (in each case 3H,s).

c) 190 g (0.55 mol) of tert.butyl 6-(2-methylidene-6,6-dimethyl-3-chlorocyclohex-1-yl)-4-oxo-hexanoate was dissolved in 1.7 l of methanol in a gasification flask, cooled to −70° and ozonized ($O_2$ flow=200 l/h) for 1 hour and 45 minutes. 108 g (1.65 mol) of $CuSO_4$-activated zinc powder, 200 ml of deionized water and 150 ml of a solution of 115 g of $K_2HPO_4$ in 300 ml of $H_2O$ was placed in a 4 l four-necked flask fitted with a stirrer, thermometer, condenser and dropping funnel. The cold ozonization mixture was rapidly added dropwise and the resulting grey suspension was heated under reflux. After 17 hours the remainder of the $K_2HPO_4$ solution was added and the mixture was heated under reflux. After 4 days the pH value of the mixture was adjusted with saturated $K_2HPO_4$ solution to ∼7, after 5 days to pH 7.5 and after 6 days to pH 8. After a total of 11 days the grey mixture was left to cool and the phases were separated. The aqueous phase was extracted 3 times with hexane. The combined organic phases were washed neutral 3 times with saturated NaCl solution, dried over $MgSO_4$ and evaporated. 84.17 g of tert.butyl 2-[5,5-dimethyl-2-oxo-2,3,4,4a,5,6,7,8- octahydronaphth-1-yl]acetate was obtained as a yellow oil.

A pure product was obtained after 2-fold distillation of this product at 130° or 170° and 0.267 mbar and chromatography on $SiO_2$.

NMR: 200 MHz ($CDCl_3$+TMS): 3.36 ppm (1H,s); 1.48 ppm (1H,dd,$J_1$=13,$J_2$=3); 1.42 ppm (9H,s); 1.055 ppm and 0.85 ppm (in each case 3H,s).

The foregoing $CuSO_4$-activated zinc powder was prepared as follows:

130 g of zinc powder was suspended in 200 ml of 0.01N HCl solution and, after decantation, washed neutral with water. Then, the zinc was added to a solution of 7.7 g of $CuSO_4$ in 200 ml of water and stirred for 2.5 hours. Thereafter, the ZnCu couple was filtered off under suction, rinsed with water, acetone and ether and dried in a drying oven at room temperature.

EXAMPLE 3

The tert.butyl 2-[5,5-dimethyl-2-oxo-2,3,4,4a,5,6, 7,8-octahydronaphth-1-yl]-acetate used as the starting material in Example 1 can also be prepared as follows:

a) 388 g (2 mol) of dihydro-α-ionone was placed in 2.2 l of methylene chloride in a 10 l four-necked flask fitted with a stirrer, thermometer, condenser and dropping funnel. Then, 660 g (4.6 mol) of potassium dihydrogen phosphate dissolved in 3 l of water was added and the resulting emulsion was cooled in an ice bath. 1.6 (2.3 mol) of sodium hypochlorite solution (~12%) was added at about 10° within 1.5 hours and, after about 3 hours at 15°, a further 350 ml (0.5 mol) was added. The pH value of the mixture was adjusted to ~5.5 with acetic acid and it was stirred at room temperature. After a total reaction time of 27 hours the phases were separated and the aqueous phase was extracted 4 times with methylene chloride. The combined organic phases were washed neutral once with water, twice with saturated $NaHCO_3$ solution and a further 3 times with water, dried over $MgSO_4$, filtered and evaporated (bath temperature=room temperature). 407.45 g 4-(3-chloro-2-methylidene-6,6-dimethyl-cyclohex-1-yl)-butan-2-one was obtained as a yellow liquid.

NMR: 200 MHz ($CDCl_3$+TMS): 5.34 ppm (1H,s); 4.78 ppm (1H,s); 4.48 ppm (1 H,dd,$J_1$=6.5,$J_2$=5); 2.12 ppm (3H,s); 0.943 and 0.86 ppm (s, in each case 3H).

b) 200 g (0.87 mol) of 4-(3-chloro-2-methylidene-6,6-dimethyl-cyclohex-1-yl)-butan-2-one [prepared according to a)] was dissolved in 1.7 l of methanol in a 3 l gasification flask, cooled to ~ −70° and ozonized ($O_2$ flow=300 l/h) for 2 hours and 15 minutes. In so doing the yellow solution became colorless and thereupon $O_2$ was blown through for 30 minutes.

165.5 g of zinc powder and 550 ml of water was placed in a 4.5 l four-necked flask fitted with a stirrer, thermometer, condenser and dropping funnel. Then, the cold ozonization mixture was added within 5 minutes and the mixture was adjusted to pH 2.5 with 25% $H_2SO_4$, whereby the temperature rises to 65°. The mixture was heated under reflux and the pH value was held constant at 2-3 with $H_2SO_4$. After 3 hours the mixture was cooled, the zinc powder was filtered off under suction and the solution was extracted 4 times with ether. The combined ether phases were washed neutral once with saturated NaCl solution, twice with saturated $NaHCO_3$ solution and again twice with saturated NaCl solution, dried over $MgSO_4$, filtered and evaporated. 145 g of 4-(2-oxo-6,6-dimethylcyclohex-1-yl)-butan-2-one was obtained as a yellow liquid.

NMR: 200 MHz ($CDCl_3$+TMS): 2.58 ppm (1H,ddd,$J_1$=17,$J_2$=9,$J_3$=5.5);2.11 ppm (3H,s); 1.085 ppm (3H,s); 0.785 ppm (3H,s).

c) 8.5 g (43.3 mmol) of 4-(2-oxo-6,6-dimethylcyclohex-1-yl)-butane-2-one was placed in 170 ml of cyclohexane under nitrogen in a 250 ml two-necked flask fitted with a magnetic stirrer, thermometer and water separator with condenser. 3.57 ml (43.3 mmol) of pyrrolidine and 100 mg (0.53 mmol) of p-toluenesulphonic acid was then added and the mixture was heated under reflux. After ~23 hours 0.73 g (5.3 mmol) of potassium carbonate was added and the cyclohexane was distilled off. The residue was distilled in a bulb-tube at 100°-110° and 0.267 mbar and 10.34 g of 5,5-dimethyl-2-N-pyrrolidinyl-3,4,4a,5,6,7-hexahydronaphthalene was obtained.

H-NMR: 200 MHz ($CDCl_3$+TMS): 5.125 ppm (1 H,m); 4.90 ppm (1H,s); 0.985 ppm (3H,s); 0.79 ppm (3H,s).

d) 9.3 g (40.2 mmol) of 5,5-dimethyl-2-N-pyrrolidinyl-3,4,4a,5,6,7-hexahydronaphthalene [obtained according to c)] was placed in 110 ml of propionitrile under argon in a 250 ml four-necked flask fitted with a stirrer, thermometer, condenser and dropping funnel. Then, 8.5 ml (48 mmol) of N-ethyldiisopropylamine and 6.6 ml (44.2 mmol) of tert.-butyl bromoacetate was added and the dark yellow solution was heated under reflux. After 10 days the dark brown mixture was left to cool, treated in an ice bath with 100 ml of acetic acid-/acetate buffer (pH 4.1) and left to react for 20 minutes. The mixture was then extracted twice with 100 ml of hexane. The organic phase was washed 10 times with 100 ml of water, dried over $MgSO_4$, filtered and evaporated. 9.93 g of tert.butyl 2-[5,5-dimethyl-2-oxo-2,3,4,4a,5,6,7,8-octahydronaphth-1-yl]-acetate was obtained.

EXAMPLE 4

In Examples 4a) to 4d) the respective component (A) situated in the first position and in parentheses relates to the reaction product of Example 1c), i.e. to the 1:1 mixture of (3aRS,5aSR)- and (3aSR,5aSR)-3a,6,6-trimethyl-1,2,3a,4,5,5a,6,7,8,9-decahydro-naphtho[2,1-b]furan (compounds of formulae Ia and Ib).

a) Tobacco flavor (Virginia type):

|  | Parts by weight: | | |
|---|---|---|---|
| (A) | — | 30.0 | 30.0 |
| Thibetolide (Ω-pentadecalactone) | 0.4 | 0.4 | 0.4 |
| Sandalwood oil | 10.0 | 10.0 | 10.0 |
| Cedarwood oil Virginia | 1.5 | 1.5 | 1.5 |
| α-Ionone | 0.1 | 0.1 | 0.1 |
| β-Ionone | 0.5 | 0.5 | 0.5 |
| Ketoisophorone | 2.0 | 2.0 | 2.0 |
| Geranyl acetate | 0.5 | 0.5 | 0.5 |
| Oleoresin ex Virginia tobacco | — | — | 100.0 |
| Ethyl alcohol | 155.0 | 155.0 | 155.0 |
| Propylene glycol | 830.0 | 800.0 | 700.0 |
|  | 1000.0 | 1000.0 | 1000.0 |

The sweetish, woody note which was clearly present was reduced by the addition of (A) to the above compositions.

When the flavored tobacco was smoked, a typical, tobacco-like, tea-like/woody note which was strongly reminiscent of Virginia tobacco appeared.

b) Men's perfume base, masculine type:

| | Parts by weight: |
|---|---|
| (A) | 70.0 |
| Benzyl acetate | 30.0 |
| Geranyl acetate | 50.0 |
| Allyl-amyl-glycolate | 3.0 |
| Methyl anthranylate | 1.0 |
| Basil oil | 10.0 |
| Bergamot essence (Calabr.) | 200.0 |
| α-Methylionone | 50.0 |
| Citrus essence (Argentin.) | 100.0 |
| Coumarin. pure cryst. | 20.0 |
| Dihydromyrcenol | 80.0 |
| Estragon oil | 5.0 |
| EVERNYL ® (methyl β-orcinecarboxylate) | 3.0 |
| FIXOLIDE ® (1,1,2,4,4,7-hexamethyl-6-acetyl-1,2,3,4-tetrahydronaphthalene) | 60.0 |
| Clove oil | 15.0 |
| HEDIONE ® (methyl dihydrojasmonate) | 50.0 |
| Isoeugenol | 3.0 |
| Lavandin oil | 100.0 |
| Methyl cedryl ketone | 60.0 |
| Nutmeg essence | 20.0 |
| Patchouli essence (iron-free) | 40.0 |
| Peche (γ-undecalactone) | 1.0 |
| Petitgrain oil Paraguay | 7.0 |
| Sandalore [3-methyl-5-(2,3,3-dimethylcyclopent-3-en-1-yl)-pentan-2-ol] | 20.0 |
| Vanillin | 2.0 |
| | 1000.0 |

By the presence of (A) in the above base, the woody note in a corresponding semi-oriental perfume (7% alcoholic solution with 90° alcohol) was intensified by its dry and natural ambergris character and more warmth in an animalic-tobacco like direction was conferred to the whole accord.

c) Perfume base, suitable for soap, flowery type:

| | Parts by weight: |
|---|---|
| (A) | 10.0 |
| Benzyl acetate | 40.0 |
| Geranyl acetate | 40.0 |
| 3-cis-Hexenyl acetate | 2.0 |
| p-tert.Butyl-cyclohexyl acetate | 60.0 |
| Cinnamic alcohol | 40.0 |
| Phenylethyl alcohol | 100.0 |
| α-Hexylcinnamaldehyde | 150.0 |
| Phenylacetaldehyde 85%/APE | 1.0 |
| Aubepine (anisaldehyde) | 5.0 |
| Bergamot essence (Calabr.) | 60.0 |
| Cedarwood essence (Virginia) | 50.0 |
| Dimethylbenzyl-carbinyl butyrate | 5.0 |
| Citronellol extra | 40.0 |
| Coumarin cryst. | 15.0 |
| δ-Decalactone | 4.0 |
| Dipropylene glycol | 20.0 |
| Ethylvanillin 10%/DIP | 2.0 |
| Eugenol (pure) | 15.0 |
| EVERNYL ® | 3.0 |
| FIXOLIDE ® | 50.0 |
| Galbanum essence | 1.0 |
| Hydroxycitronellal | 30.0 |
| Indolene | 2.0 |
| LILIAL ® | 40.0 |
| Mandarin essence | 10.0 |
| Methyl-diantilis (ethylvanillyl methyl ether) | 10.0 |
| Nonadyl | 30.0 |
| Amyl salicylate | 50.0 |
| Benzyl salicylate | 80.0 |
| α-Terpinol | 30.0 |
| Undecavertol (4-methyl-dec-3-en-5-ol) | 5.0 |
| | 1000.0 |

The presence of (A) in the above composition led to a warm, animalic-amber like tonality of the natural ambergris type, the spicy note underlining and intensifying the tobacco character.

d) Perfume base for cosmetics:

| | Parts by weight: |
|---|---|
| (A) | 50.0 |
| Benzyl acetate | 40.0 |
| Dimethylbenzyl-carbinyl acetate | 40.0 |
| Geranyl acetate | 30.0 |
| Phenylethyl alcohol | 100.0 |
| Bergamot essence (Calabr.) | 100.0 |
| α-Methylionone | 80.0 |
| Cyclohexal | 40.0 |
| Dipropylene glycol | 50.0 |
| Eugenol | 20.0 |
| Galaxolide 50 DEP (1,3,4,6,7,8-hexahydro-4,6,6,7,8,8-hexamethyl-cyclopenta-γ-2-benzopyran) | 40.0 |
| Gardenol (methyl phenyl-carbinyl acetate) | 10.0 |
| Geraniol (pure) | 50.0 |
| HEDIONE ® (methyl dihydrojasmonate) | 40.0 |
| Heliotropin cryst. | 20.0 |
| Hydroxycitronellal | 50.0 |
| Methyl cedryl ketone | 60.0 |
| Methylisoeugenol | 10.0 |
| Musk ketone | 50.0 |
| Benzyl salicylate | 100.0 |
| Thibetolide | 20.0 |
| | 1000.0 |

In this flowery accord for creams the presence of (A) conferred to the whole a more sensuous skin care note by a combination of its ambergris character with the musk substances which were used.

I claim:

1. Naphthofuran derivatives of the formula

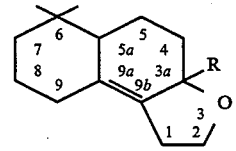

I wherein R represents hydrogen, methyl or ethyl.

2. Naphthofuran derivatives according to claim 1 of the formulae

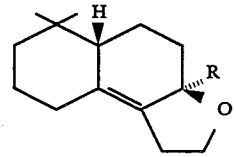

Ia

and

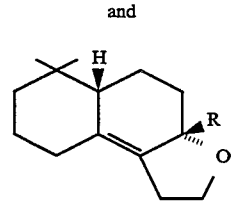

Ib where R represents hydrogen, methyl or ethyl, as well as their respective enantiomers and mixtures thereof.

3. Naphthofuran derivatives of formula Ia and Ib according to claim 2, wherein R signifies methyl.

4. A process for the manufacture of the compounds of formula

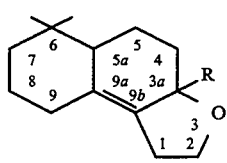

wherein R represents hydrogen, methyl or ethyl, which process comprises cyclizing a compound of the formula

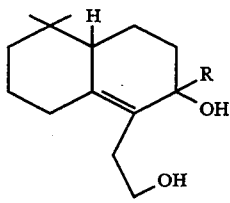

wherein R is as above.

5. The process of claim 4, wherein R is hydrogen.

6. An odorant and/or flavor composition which comprises a compound according to claim 1.

7. The odorant and/or flavor composition of claim 6, wherein the compound comprises at least one naphthofuran derivative of the formulae

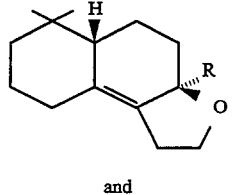

and

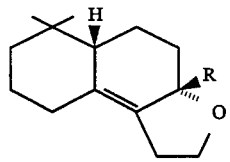

where R represents hydrogen, methyl or ethyl, as well as their respective enantiomers and mixtures thereof.

8. The composition according to claim 7, wherein R signifies methyl.

9. A method of improving the olfactory properties of odorant and flavor compositions, comprising incorporating a naphthofuran derivative according to claim 1.

* * * * *